US012630495B2

(12) United States Patent
Minakar et al.

(10) Patent No.: US 12,630,495 B2
(45) Date of Patent: May 19, 2026

(54) METHOD FOR PRODUCING ESTERS OF HOMOVANILLIC ACID

(71) Applicant: SYMRISE AG, Holzminden (DE)

(72) Inventors: Amin Minakar, Neustadt an der Weinstrasse (DE); Michael Backes, Holzminden (DE); Diego Jaime, Holzminden (DE); Melvin Huckauf, Holzminden (DE)

(73) Assignee: SYMRISE AG, Holzminden (DE)

( * ) Notice: Subject to any disclaimer, the term of this patent is extended or adjusted under 35 U.S.C. 154(b) by 859 days.

(21) Appl. No.: 17/996,957

(22) PCT Filed: Apr. 27, 2020

(86) PCT No.: PCT/EP2020/061598
§ 371 (c)(1),
(2) Date: Oct. 24, 2022

(87) PCT Pub. No.: WO2021/219192
PCT Pub. Date: Nov. 4, 2021

(65) Prior Publication Data

US 2023/0167045 A1 Jun. 1, 2023

(51) Int. Cl.
*C07C 67/08* (2006.01)
*C07C 67/03* (2006.01)

(52) U.S. Cl.
CPC .............. *C07C 67/08* (2013.01); *C07C 67/03* (2013.01)

(58) Field of Classification Search
None
See application file for complete search history.

(56) References Cited

FOREIGN PATENT DOCUMENTS

| | | | |
|---|---|---|---|
| CN | 104262292 | A | 1/2015 |
| WO | 2007009590 | A1 | 1/2007 |

OTHER PUBLICATIONS

International Search Report and Written Opinion issued on Dec. 7, 2020 for corresponding PCT Application No. PCT/EP2020/061598.
Barbara Leider et al., "Biological Evaluation of Natural and Synthesized Homovanillic Acid Esters as Inhibitors of Intestinal Fatty Acid Uptake in Differentiated Caco-2 Cells," Molecules, vol. 24, No. 19, 2019, p. 3599 XP055753324.
Jacqueline E. Milne et al., "Iodite-Catalyzed Reductions: Development of a Synthesis of Phenylacetic Acids," Journal of Organic Chemistry, vol. 76, No. 22, 2011, pp. 9519-9524 XP055753296.
Barbara Lieder et al.; "Biological Evaluation of Natural and Synthesized Homovanillic Acid Esters as Inhibitors of Intestinal Fatty Acid Uptake in Differentiated Caco-2 Cells," Molecules, 2019, vol. 24, 2019; pp. 1-14.
Jacqueline E. Milne et al.; "Iodide-Catalyzed Reductions: Development of a Synthesis of Phenylacetic Acids," The Journal of Organic Chemistry, vol. 76, 2011, pp. 9519-9524.

*Primary Examiner* — Amy C Bonaparte
(74) *Attorney, Agent, or Firm* — POLSINELLI PC

(57) ABSTRACT

The present invention primarily relates to a method for producing a compound of formula (I) and/or a physiologically acceptable salt thereof from vanillylmandelic acid and/or a physiologically acceptable salt thereof. The present invention further relates to the simultaneous use of one or more iodide salt(s) or hydrate(s) thereof, one or more reducing agent(s), one or more inorganic and/or organic acid(s) other than phosphonic acid, and methanol and/or a physiologically acceptable salt thereof or an alcohol of formula (II) as defined herein and/or a physiologically acceptable salt thereof for converting vanillylmandelic acid and/or a physiologically acceptable salt thereof into a compound of formula (I) and/or a physiologically acceptable salt thereof or into a compound of formula (III) as defined herein and/or a physiologically acceptable salt thereof.

20 Claims, No Drawings

METHOD FOR PRODUCING ESTERS OF HOMOVANILLIC ACID

CROSS-REFERENCE TO RELATED APPLICATIONS

This application is a national stage application (under 35 U.S.C. § 371) of PCT/EP2020/061598, filed Apr. 27, 2020, which is incorporated herein by reference in its entirety.

The present invention primarily relates to a method for producing a compound of formula (I) as defined herein and/or a physiologically acceptable salt thereof from vanillylmandelic acid and/or a physiologically acceptable salt thereof. The present invention further relates to the simultaneous use of one or more iodide salt(s) or hydrate(s) thereof, one or more reducing agent(s), one or more inorganic and/or organic acid(s) other than phosphonic acid, and methanol and/or a physiologically acceptable salt thereof or an alcohol of formula (II) as defined herein and/or a physiologically acceptable salt thereof for converting vanillylmandelic acid and/or a physiologically acceptable salt thereof into a compound of formula (I) and/or a physiologically acceptable salt thereof or into a compound of formula (III) as defined herein and/or a physiologically acceptable salt thereof.

Further aspects of the present invention will arise from the description below, in particular from the examples, as well as from the attached patent claims.

Alkyl esters of homovanillic acid, especially ethyl homovanillate, were first identified during screening reactions of ascorbic acid with various flavouring substances. In 2009, the methyl ester of homovanillic acid was found in the wood of oak barrels, which normally contain wine and spirits. Later, it could be shown that ethyl homovanillate also occurs in nature and can be found e.g. in wine stored in oak barrels (Fernandez de Simon, B.; Esteruelas, E.; Munoz, A. M.; Cadahia, E.; Sanz, M., *J. Agric. Food Chem.* 2009, 57, 3217-3227; Cabaroglu, T.; Canbas, A.; Baumes, R.; Bayonove, C.; Lepoutre, J. P.; Günata, Z., *J. Food Sci.* 1997, 62, 680-692; van Jaarsveld, F. P.; Hattingh, S.; Minnaar, P., S. Afr. *J. Enol. Vitic.* 2009, 30, 24-37).

Esters of homovanillic acid are used
- as flavouring agents with a pungent or warming effect, and/or
- as flavouring agents for reducing or masking an unpleasant taste impression, preferably in the sensory context of astringent, bitter, dry, dusty, floury, chalky, floury, and metallic, and/or
- as flavouring agents for enhancing a pleasant taste impression, preferably selected from the group consisting of warming, pungent and cooling (WO 2015/158677 A1).

Moreover, patent application US 2009/0170942 A1 describes in detail certain homovanillic acid ester derivatives and their diverse applications, e.g. in the medical field.

Patent application WO 2015/158677 A1 describes a synthesis of esters of homovanillic acid based on the treatment of homovanillic acid with the corresponding alcohols. Because of the high price and the difficult access to homovanillic acid, an alternative synthesis route towards esters of homovanillic acid is described in EP 1509492. The multi-step process described therein includes the transformation of vanillylmandelic acid under high temperatures and basic conditions to the corresponding homovanillic acid in the presence of catalytic amounts of palladium on charcoal. After several work-up and purification steps, the isolated carboxylic acid is treated with alcohols to isolate certain esters of homovanillic acid.

The main drawbacks of the production methods for esters of homovanillic acid as described in the prior art are:
- The undesired formation of vanillin as side product during the synthesis, which has a significant and undesired effect on the taste of the product,
- high costs,
- complex multi-stage processes and several work-up and purification steps,
- long reaction times,
- the use of palladium, which necessitates extensive work-up after synthesis of the raw product,
- low yield, and
- insufficient purity of the product.

Thus, it was an object of the present invention to provide an optimized synthetic strategy towards a broad range of esters of homovanillic acid that would avoid the drawbacks as described above. Further objects underlying the present invention follow from the description below and the present patent claims.

Milne et al., for instance, describe the synthesis of phenylacetic acids via the iodide-catalysed reduction of mandelic acids. The procedure relies on the in situ generation of hydroiodic acid from catalytic sodium iodide, employing phosphonic acid as a stoichiometric reductant (Milne, J. E.; Storz, T.; Colyer, J. T.; Thiel, O. R.; Dilmeghani Seran, M.; Larsen, R. D.; Murry; J. A.; *J. Org. Chem.* 2011, 76, 9619-9524.). The synthesis of any esters, however, is not described in said document.

According to a first aspect of the present invention, the stated object is achieved by a method for producing a compound of formula (I) and/or a physiologically acceptable salt thereof, (I)

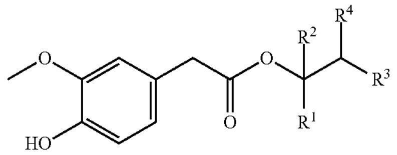

comprising or consisting of the following step(s):

(a) simultaneously reacting vanillylmandelic acid and/or a physiologically acceptable salt thereof
with
- one or more iodide salt(s) or hydrate(s) thereof,
- one or more reducing agent(s), preferably phosphonic acid,
- one or more inorganic and/or organic acid(s) other than phosphonic acid, and
- methanol and/or a physiologically acceptable salt thereof or an alcohol of formula (II) and/or a physiologically acceptable salt thereof (II)

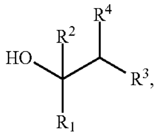

and (b) provided that methyl-2-(4-hydroxy-3-methoxy-phenyl)acetate of formula (III) (methyl homovanillate or methyl ester of homovanillic acid; within the framework of the present text also designated "compound of formula (III)")

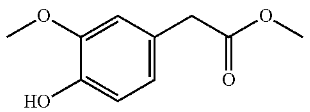

(III)

and/or a physiologically acceptable salt thereof is obtained in step (a), subjecting said compound of formula (III) and/or salt thereof and an alcohol of formula (II) and/or a physiologically acceptable salt thereof to a transesterification reaction to obtain a compound of formula (I) and/or a physiologically acceptable salt thereof, or provided that a compound of formula (I) and/or a physiologically acceptable salt thereof is obtained in step (a), optionally subjecting said compound of formula (I) and/or salt thereof obtained in step (a) and an alcohol of formula (II) that is different from the alcohol of formula (II) of step (a) and/or a physiologically acceptable salt thereof to a transesterification reaction, wherein in the compound of formula (I) (and, if applicable, in the salt thereof) and in the alcohol of formula (II) (and, if applicable, in the salt thereof), respectively, (i) $R^1$ and $R^2$ independently represent hydrogen or an alkyl residue with 1-2 carbon atoms, and $R^3$ and $R^4$ independently represent a residue selected from the group consisting of hydrogen, linear or branched alkyl with 1-5 carbon atoms, phenyl, alkylphenyl, phenylalkyl, linear or branched alkenyl with 2-4 carbon atoms, alkenylphenyl and phenylalkenyl, or (ii) $R^1$ and $R^3$ form a cyclohexyl ring together with the carbon atoms that link them, the cyclohexyl ring optionally carrying a residue $R^5$, wherein $R^5$ represents an alkyl residue with 1-2 carbon atoms, and $R^2$ represents hydrogen or an alkyl residue with 1-2 carbon atoms, and $R^4$ represents a residue selected from the group consisting of hydrogen, linear or branched alkyl with 1-5 carbon atoms, phenyl, alkylphenyl, phenylalkyl, linear or branched alkenyl with 2-4 carbon atoms, alkenylphenyl and phenylalkenyl.

Vanillylmandelic acid has the following chemical structure:

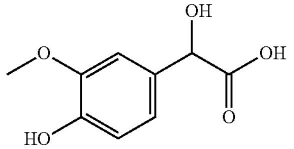

Examples of physiologically acceptable salts of methanol, vanillylmandelic acid, the compounds of formula (I), the alcohols of formula (II) and the compound of formula (III) as defined herein include lithium, sodium, potassium, magnesium, calcium and ammonium salts.

According to one embodiment, methanol and/or a physiologically acceptable salt thereof may be used as alcohol component in step (a) of the method according to the invention. In case methanol is used in step (a) of the method according to the invention, methyl-2-(4-hydroxy methoxyphenyl)acetate of formula (III) and/or a physiologically acceptable salt thereof is/are obtained as product of step (a). Consequently, step (b) of the method according to the invention has to be carried out, wherein the compound of formula (III) and/or a physiologically acceptable salt thereof and an alcohol of formula (II) and/or a physiologically acceptable salt thereof are subjected to a transesterification reaction to obtain a compound of formula (I) and/or a physiologically acceptable salt thereof.

According to another embodiment, an alcohol of formula (II) and/or a physiologically acceptable salt thereof may be used as alcohol component in step (a) of the method according to the invention. In case an alcohol of formula (II) and/or a physiologically acceptable salt thereof is used in step (a) of the method according to the invention, a compound of formula (I) and/or a physiologically acceptable salt thereof is obtained as product in step (a).

Thus, according to a preferred embodiment, the method according to the invention does not contain step (b) and the compound of formula (I) and/or a physiologically acceptable salt thereof is obtained via step (a) only.

According to another embodiment, the compound of formula (I) and/or a physiologically acceptable salt thereof as obtained in step (a) of the method according to the invention may be subjected to a transesterification reaction to obtain a different compound of formula (I) and/or a physiologically acceptable salt thereof in step (b) of the reaction according to the invention. This embodiment is particularly advantageous when a particular alcohol of formula (II) and/or a physiologically acceptable salt thereof is expensive. In this case, the method according to the invention is preferably carried out such that a less expensive alcohol of formula (II) and/or a physiologically acceptable salt thereof is used in step (a) and the more expensive alcohol of formula (II) and/or a physiologically acceptable salt thereof is used in the transesterification step (b) of the method according to the invention leading to a compound of formula (I) and/or a physiologically acceptable salt thereof, which is an ester of homovanillic acid and the more expensive alcohol of compound (II) used in step (b).

Particularly preferred less expensive alcohols of formula (II) for use in step (a) of the method according to the invention, which may be replaced by a more expensive alcohol of formula (II) in step (b) of the method, are for example ethanol, isopropanol, 2-butanol, 2-methylpropan ol, 2-methylbutan-1-ol, heptanol, 2-hexanol, 2-heptanol, propanol, 3-methylbutan-1-ol, 2-methylbutan-2-ol, butanol, pentanol and hexanol. Moreover, a particularly preferred alcohol for use in step (a) of the method according to the invention, which may be replaced by a more expensive alcohol of formula (II) in step (b) of the method, is methanol.

According to a preferred embodiment, the transesterification reaction in step (b) of the method according to the invention, if present, is carried out in the presence of a catalytic amount of one or more acid(s). Particularly preferred acids for this purpose are e.g. methanesulfonic acid, p-toluenesulfonic acid, sulfuric acid, phosphoric acid and acidic ion exchange resins.

According to a preferred embodiment, the transesterification reaction in step (b) of the method according to the invention, if present, is carried out under the following reaction conditions: 1 equivalent of the compound of formula (III) and/or of the salt thereof or 1 equivalent of the compound of formula (I) and/or of the salt thereof is treated with catalytic amounts of 0.01-0.2 equivalents, preferably 0.03-0.15 equivalents, of one or more acid(s) in the presence of 0.8-1.4 equivalents, preferably 1.0-1.2 equivalents, of an alcohol of formula (II) and/or a salt thereof (if applicable, an alcohol of formula (II) and/or a salt thereof that is different from the one used in step (a) of the method according to the invention) at 70° C.-100° C., preferably at 80° C.-95° C., and under vacuum at 150-250 mbar, preferably at 190-210 mbar. The reaction mixture is stirred for 30-40 minutes before the solution is warmed up to 115-150° C., preferably to 125-140° C., at 100-200 mbar, preferably at 130-170 mbar, and stirred further for 10-12 hours. After the addition of soda at room temperature, the starting material and alcohol(s) are distilled off under reduced pressure and at 160-180° C., preferably at 165-175° C., to obtain the (different) compound of formula (I) and/or salt thereof.

Preferably, the compounds of formula (I) (and/or salts thereof) are isolated from the obtained reaction mixture by distillation, preferably short path distillation, after step (a) and/or step (b) of the method according to the invention.

The method according to the invention is particularly advantageous, because

- the obtained product is free of the side-product vanillin,
- no heavy metals are required as catalysts and hence the work-up procedure is simplified,
- large scale synthesis is possible in a convenient one-pot process,
- high yield and purity of the products can be achieved,
- the production costs are considerably lower compared to methods of the prior art,
- the reaction time is shorter compared to methods of the prior art, and
- it enables the synthesis of a wide range of compounds of formula (I) (and/or salts thereof).

A preferred embodiment according to the invention is a method as defined herein, wherein a total amount of 0.1-1 equivalents, preferably of 0.25-0.95 equivalents, more preferably of 0.35-0.85 equivalents, of the one or more iodide salt(s) or hydrate(s) thereof is reacted in step (a) based on 1 equivalent of the vanillylmandelic acid and/or salt thereof.

Preferably, a total amount of 0.1-1 equivalents, preferably of 0.25-0.95 equivalents, more preferably of 0.35-0.85 equivalents, of one iodide salt (as defined herein further below) is reacted in step (a) based on 1 equivalent of the vanillylmandelic acid and/or salt thereof.

Another preferred embodiment according to the invention is a method as defined herein, wherein a total amount of 0.5-2 equivalents, preferably of 0.8-1.7 equivalents, more preferably of 0.9-1.2 equivalents, of the one or more reducing agent(s), preferably of the phosphonic acid, is reacted in step (a) based on 1 equivalent of the vanillylmandelic acid and/or salt thereof.

Preferably, a total amount of 0.5-2 equivalents, preferably of 0.8-1.7 equivalents, more preferably of 0.9-1.2 equivalents, of one reducing agent is reacted in step (a) based on 1 equivalent of the vanillylmandelic acid and/or salt thereof.

Most preferably, a total amount of 0.5-2 equivalents, preferably of 0.8-1.7 equivalents, more preferably of 0.9-1.2 equivalents, of phosphonic acid is reacted in step (a) based on 1 equivalent of the vanillylmandelic acid and/or salt thereof.

Another preferred embodiment according to the invention is a method as defined herein, wherein a total amount of 0.1-2 equivalents, preferably of 0.2-1.7 equivalents, more preferably of 0.3-1.5 equivalents, of the one or more inorganic and/or organic acid(s) is reacted in step (a) based on 1 equivalent of the vanillylmandelic acid and/or salt thereof.

Preferably, a total amount of 0.1-2 equivalents, preferably of 0.2-1.7 equivalents, more preferably of 0.3-1.5 equivalents, of one inorganic acid is reacted in step (a) based on 1 equivalent of the vanillylmandelic acid and/or salt thereof.

Preferably, a total amount of 0.1-2 equivalents, preferably of 0.2-1.7 equivalents, more preferably of 0.3-1.5 equivalents, of one organic acids is reacted in step (a) based on 1 equivalent of the vanillylmandelic acid and/or salt thereof.

Another preferred embodiment according to the invention is a method as defined herein, wherein a total amount of 2-20 equivalents, preferably of 3-16 equivalents, more preferably of 4-12 equivalents, of the methanol and/or salt thereof or alcohol of formula (II) and/or salt thereof is reacted in step (a) based on 1 equivalent of the vanillylmandelic acid and/or salt thereof.

Preferably, a total amount of 2-20 equivalents, preferably of 3-16 equivalents, more preferably of 4-12 equivalents, of the alcohol of formula (II) and/or salt thereof (as defined herein further below) is reacted in step (a) based on 1 equivalent of the vanillylmandelic acid and/or salt thereof.

Preferably, a total amount of 2-20 equivalents, preferably of 3-16 equivalents, more preferably of 4-12 equivalents, of methanol and/or salt thereof is reacted in step (a) based on 1 equivalent of the vanillylmandelic acid and/or salt thereof.

Another preferred embodiment according to the invention is a method as defined herein, wherein the reaction in step (a) is carried out at 60-100° C., preferably at 70-95° C., more preferably at 75-90° C.

Another preferred embodiment according to the invention is a method as defined herein, wherein the reaction in step (a) is carried out over the course of 2-6 hours, preferably 3-5 hours, more preferably at 3.5-4.5 hours.

Another preferred embodiment according to the invention is a method as defined herein, wherein the one or more iodide salt(s) or hydrate(s) thereof is/are selected from the group consisting of magnesium iodide, magnesium iodide hydrate, potassium iodide, potassium iodide hydrate, ammonium iodide, ammonium iodide hydrate, sodium iodide, sodium iodide hydrate, lithium iodide and lithium iodide hydrate, preferably wherein the iodide salt is sodium iodide.

The term "hydrate of an iodide salt" as used in the framework of the present text refers to monohydrates, dihydrates, trihydrates, tetrahydrates, pentahydrates, hexahydrates, heptahydrates, octahydrates or higher hydrates of the defined iodide salt.

Another preferred embodiment according to the invention is a method as defined herein, wherein the one or more inorganic and/or organic acid(s) is/are selected from the group consisting of sulfuric acid, preferably concentrated sulfuric acid, methanesulfonic acid, p-toluenesulfonic acid, preferably p-toluenesulfonic acid monohydrate, and hydrochloric acid, preferably wherein the inorganic and/or organic acid is methanesulfonic acid.

Another preferred embodiment according to the invention is a method as defined herein, wherein the alcohol of formula (II) is selected from the group consisting of ethanol, 2-phenylethanol, (E)-3-phenylprop-2-en-1-ol, hexan-3-ol, 3-methylbut-2-en-1-ol, (E)-hex-2-en-1-ol, (Z)-hex-3-en-1-ol, propan-2-ol, butan-2-ol, 2-methylpropan-1-ol, 2-methylbutan-2-ol, 3-methylbutan-1-ol, 2-methylbutan-1-ol, hexan-2-ol, heptan-1-ol, heptan-2-ol, 2-isopropyl-5-methylcyclohexanol, propan-1-ol, butan-1-ol, pentan-1-ol, hexan-1-ol, 3-phenylpropan-1-ol and 4-phenylbutan-1-ol.

As described above, the alcohol of formula (II) as defined herein and/or the salt thereof may be used only in step (a) of the method according to the invention (whereby step (b) of the method according to the invention is optional and may be omitted) or it may be used only in the transesterification reaction as defined in step (b) of the method according to the invention (when methanol and/or a salt thereof is used as alcohol in step (a) of the method according to the invention) or it may be used in both steps (a) and (b) to transform one compound of formula (I) and/or a salt thereof into another compound of formula (I) and/or a salt thereof via transesterification.

Examples of compounds of formula (I), that may be produced with the method according to the invention, are listed in the following:

1

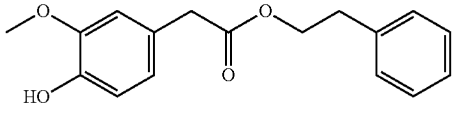

2-Phenylethyl-2-(4-hydroxy-3-methoxy-phenyl)acetate (1)

2

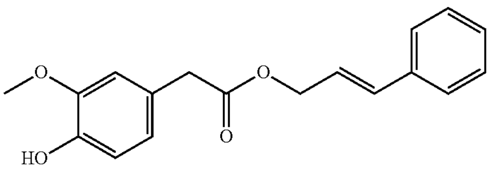

[(E)-Cinnamyl]-2-(4-hydroxy-3-methoxy-phenyl)acetate (2)

3

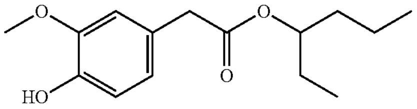

1-Ethylbutyl-2-(4-hydroxy-3-methoxy-phenyl)acetate (3)

4

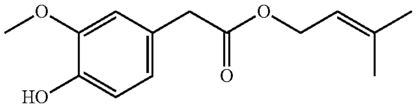

3-Methylbut-2-enyl-2-(4-hydroxy-3-methoxy-phenyl)acetate (4)

5

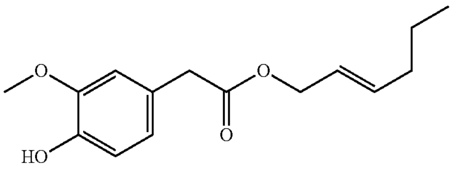

[(E)-Hex-2-enyl]-2-(4-hydroxy-3-methoxy-phenyl)acetate (5)

6

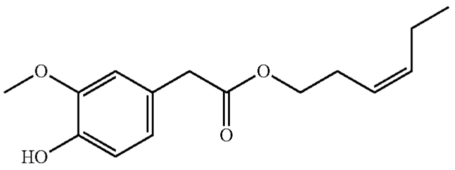

[(Z)-Hex-3-enyl]-2-(4-hydroxy-3-methoxy-phenyl)acetate (6)

7

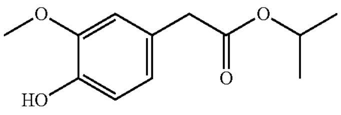

Isopropyl-2-(4-hydroxy-3-methoxy-phenyl)acetate (7)

-continued

8

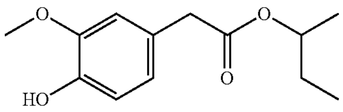

sec-Butyl-2-(4-hydroxy-3-methoxy-phenyl)acetate (8)

9

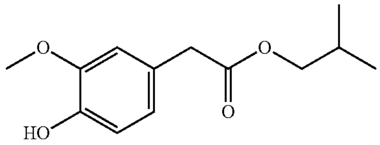

iso-Butyl-2-(4-hydroxy-3-methoxy-phenyl)acetate (9)

10

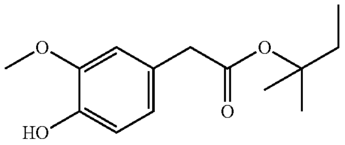

1,1-Dimethylpropyl 2-(4-hydroxy-3-methoxy-phenyl)acetate (10)

11

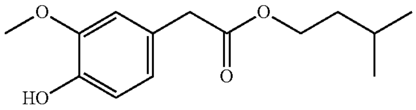

iso-Pentyl-2-(4-hydroxy-3-methoxy-phenyl)acetate (11)

12

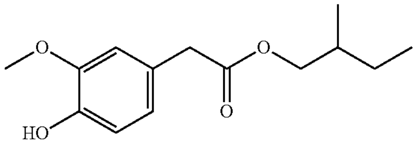

2-Methylbutyl-2-(4-hydroxy-3-methoxy-phenyl)acetate (12)

13

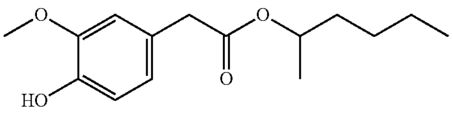

1-Methylpentyl-2-(4-hydroxy-3-methoxy-phenyl)acetat (13)

14

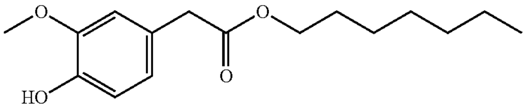

Heptyl-2-(4-hydroxy-3-methoxy-phenyl)acetate (14)

15

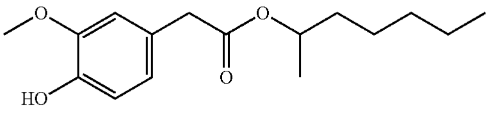

1-Methylhexyl-2-(4-hydroxy-3-methoxy-phenyl)acetate (15)

-continued

16

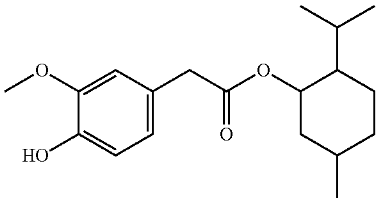

(2-iso-Propyl-5-methyl-cyclohexyl)-2-(4-hydroxy-3-methoxy-phenyl)acetate (16)

17

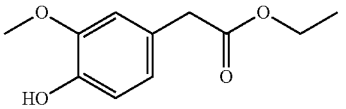

Ethyl-2-(4-hydroxy-3-methoxy-phenyl)acetate (17)

18

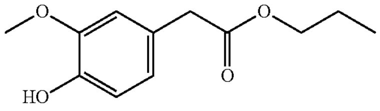

Propyl-2-(4-hydroxy-3-methoxy-phenyl)acetate (18)

19

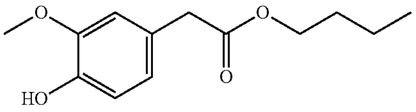

Butyl-2-(4-hydroxy-3-methoxy-phenyl)acetate (19)

20

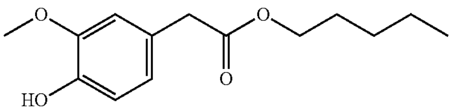

Pentyl-2-(4-hydroxy-3-methoxy-phenyl)acetate (20)

21

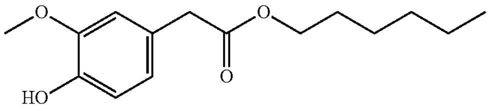

Hexyl-2-(4-hydroxy-3-methoxy-phenyl)acetate (21)

22

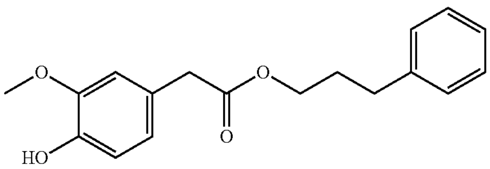

3-Phenylpropyl 2-(4-hydroxy-3-methoxy-phenyl)acetate (22)

23

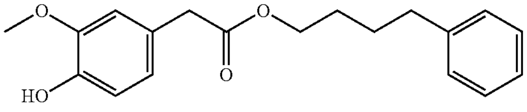

4-Phenylbutyl 2-(4-hydroxy-3-methoxy-phenyl)acetate (23)

Another embodiment of the present invention is a method for producing a pharmaceutical preparation, a preparation used in nutrition, oral hygiene or consumed for pleasure comprising a method step as defined above.

A particularly preferred embodiment of the present invention is a method for producing a pharmaceutical preparation, a preparation used in nutrition, oral hygiene or consumed for pleasure comprising method step (a) as defined above.

Another particularly preferred embodiment of the present invention is a method for producing a pharmaceutical preparation, a preparation used in nutrition, oral hygiene or consumed for pleasure comprising both method steps (a) and (b) as defined above.

A second aspect of the present invention relates to the simultaneous use of

- one or more iodide salt(s) or hydrate(s) thereof,
- one or more reducing agent(s), preferably of phosphonic acid,
- one or more inorganic and/or organic acid(s) other than phosphonic acid, and
- methanol and/or a physiologically acceptable salt thereof or an alcohol of formula (II) and/or a physiologically acceptable salt thereof.

(II)

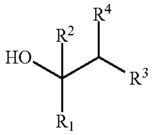

for converting vanillylmandelic acid and/or a physiologically acceptable salt thereof into a compound of formula (I) and/or a physiologically acceptable salt thereof or into methyl-2-(4-hydroxy-3-methoxy-phenyl)acetate of formula (III) and/or a physiologically acceptable salt thereof, (I)

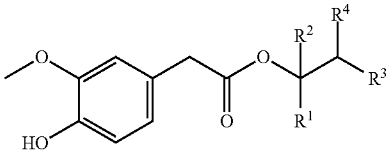

(III)

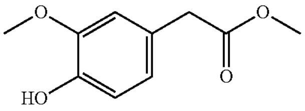

wherein in the compound of formula (I) (and, if applicable, in the salt thereof) and in the alcohol of formula (II) (and, if applicable, in the salt thereof), respectively, (i) $R^1$ and $R^2$ independently represent hydrogen or an alkyl residue with 1-2 carbon atoms, and
$R^3$ and $R^4$ independently represent a residue selected from the group consisting of hydrogen, linear or branched alkyl with 1-5 carbon atoms, phenyl, alkylphenyl, phenylalkyl, linear or branched alkenyl with 2-4 carbon atoms, alkenylphenyl and phenylalkenyl, or (ii) $R^1$ and $R^3$ form a cyclohexyl ring together with the carbon atoms that link them, the cyclohexyl ring optionally carrying a residue $R^5$, wherein $R^5$ represents an alkyl residue with 1-2 carbon atoms, and
$R^2$ represents hydrogen or an alkyl residue with 1-2 carbon atoms, and
$R^4$ represents a residue selected from the group consisting of hydrogen, linear or branched alkyl with 1-5 carbon atoms, phenyl, alkylphenyl, phenylalkyl, linear or branched alkenyl with 2-4 carbon atoms, alkenylphenyl and phenylalkenyl.

A preferred embodiment according to the invention is a use as defined herein, wherein a total amount of 0.1-1 equivalents, preferably of 0.25-0.95 equivalents, more preferably of 0.35-0.85 equivalents, of the one or more iodide salt(s) or hydrate(s) thereof is used based on 1 equivalent of the vanillylmandelic acid and/or salt thereof.

Preferably, a total amount of 0.1-1 equivalents, preferably of 0.25-0.95 equivalents, more preferably of 0.35-0.85 equivalents, of one iodide salt (as defined herein further below) is used based on 1 equivalent of the vanillylmandelic acid and/or salt thereof.

Another preferred embodiment according to the invention is a use as defined herein, wherein a total amount of 0.5-2 equivalents, preferably of 0.8-1.7 equivalents, more preferably of 0.9-1.2 equivalents, of the one or more reducing agent(s), preferably of phosphonic acid, is used based on 1 equivalent of the vanillylmandelic acid and/or salt thereof.

Preferably, a total amount of 0.5-2 equivalents, preferably of 0.8-1.7 equivalents, more preferably of 0.9-1.2 equivalents, of one reducing agent is used based on 1 equivalent of the vanillylmandelic acid and/or salt thereof.

Most preferably, a total amount of 0.5-2 equivalents, preferably of 0.8-1.7 equivalents, more preferably of 0.9-1.2 equivalents, of phosphonic acid is used based on 1 equivalent of the vanillylmandelic acid and/or salt thereof.

Another preferred embodiment according to the invention is a use as defined herein, wherein a total amount of 0.1-2 equivalents, preferably of 0.2-1.7 equivalents, more preferably of 0.3-1.5 equivalents, of the one or more inorganic and/or organic acid(s) is used based on 1 equivalent of the vanillylmandelic acid and/or salt thereof.

Preferably, a total amount of 0.1-2 equivalents, preferably of 0.2-1.7 equivalents, more preferably of 0.3-1.5 equivalents, of one inorganic acids is used based on 1 equivalent of the vanillylmandelic acid and/or salt thereof.

Preferably, a total amount of 0.1-2 equivalents, preferably of 0.2-1.7 equivalents, more preferably of 0.3-1.5 equivalents, of one organic acids is used based on 1 equivalent of the vanillylmandelic acid and/or salt thereof.

Another preferred embodiment according to the invention is a use as defined herein, wherein a total amount of 2-20 equivalents, preferably of 3-16 equivalents, more preferably of 4-12 equivalents, of the methanol and/or salt thereof or alcohol of formula (II) and/or salt thereof is used based on 1 equivalent of the vanillylmandelic acid and/or salt thereof.

Preferably, a total amount of 2-20 equivalents, preferably of 3-16 equivalents, more preferably of 4-12 equivalents, of the alcohol of formula (II) (as defined herein further below) and/or salt thereof is used based on 1 equivalent of the vanillylmandelic acid and/or salt thereof.

Preferably, a total amount of 2-20 equivalents, preferably of 3-16 equivalents, more preferably of 4-12 equivalents, of methanol and/or salt thereof is used based on 1 equivalent of the vanillylmandelic acid and/or salt thereof.

Another preferred embodiment according to the invention is a use as defined herein, wherein the conversion takes place at 60-100° C., preferably at 70-95° C., more preferably at 75-90° C.

Another preferred embodiment according to the invention is a use as defined herein, wherein the conversion is carried out over the course of 2-6 hours, preferably 3-5 hours, more preferably at 3.5-4.5 hours.

Another particularly preferred embodiment according to the invention is a use as defined herein, wherein the one or more iodide salt(s) or hydrate(s) thereof is/are selected from the group consisting of magnesium iodide, magnesium iodide hydrate, potassium iodide, potassium iodide hydrate, ammonium iodide, ammonium iodide hydrate, sodium iodide, sodium iodide hydrate, lithium iodide and lithium iodide hydrate, preferably wherein the iodide salt is sodium iodide, and/or wherein the one or more inorganic and/or organic acid(s) is/are selected from the group consisting of sulfuric acid, preferably concentrated sulfuric acid, methanesulfonic acid, p-toluenesulfonic acid, preferably p-toluenesulfonic acid monohydrate, and hydrochloric acid, preferably wherein the inorganic and/or organic acid is methanesulfonic acid, and/or wherein the alcohol of formula (II) is selected from the group consisting of ethanol, 2-phenylethanol, (E)-3-phenylprop-2-en-1-ol, hexan-3-ol, 3-methylbut-2-en-1-ol, (E)-hex-2-en-1-ol, (Z)-hex-3-en-1-ol, propan-2-ol, butan-2-ol, 2-methylpropan-1-ol, 2-methylbutan-2-ol, 3-methylbutan-1-ol, 2-methylbutan-1-ol, hexan-2-ol, heptan-1-ol, heptan-2-ol, 2-isopropyl-5-methyl-cyclohexanol, propan-1-ol, butan-1-ol, pentan-1-ol, hexan-1-ol, 3-phenylpropan-1-ol and 4-phenylbutan-1-ol.

Another particularly preferred embodiment according to the invention is a use as defined herein, wherein the one or more iodide salt(s) or hydrate(s) thereof is/are selected from the group consisting of magnesium iodide, magnesium iodide hydrate, potassium iodide, potassium iodide hydrate, ammonium iodide, ammonium iodide hydrate, sodium iodide, sodium iodide hydrate, lithium iodide and lithium iodide hydrate, preferably wherein the iodide salt is sodium iodide.

Another particularly preferred embodiment according to the invention is a use as defined herein, wherein the one or more inorganic and/or organic acid(s) is/are selected from the group consisting of sulfuric acid, preferably concentrated sulfuric acid, methanesulfonic acid, p-toluenesulfonic acid, preferably p-toluenesulfonic acid monohydrate, and hydrochloric acid, preferably wherein the inorganic and/or organic acid is methanesulfonic acid.

Another particularly preferred embodiment according to the invention is a use as defined herein, wherein the alcohol of formula (II) is selected from the group consisting of ethanol, 2-phenyl ethanol, (E)-3-phenylprop-2-en-1-ol, hexan-3-ol, 3-methylbut-2-en-1-ol, (E)-hex-2-en-1-ol, (Z)-hex-3-en-1-ol, propan-2-ol, butan-2-ol, 2-methylpropan-1-ol, 2-methylbutan-2-ol, 3-methylbutan-1-ol, 2-methylbutan-1-ol, hexan-2-ol, heptan-1-ol, heptan-2-ol, 2-isopropyl-5-methyl-cyclohexanol, propan-1-ol, butan-1-ol, pentan-1-ol, hexan-1-ol, 3-phenylpropan-1-ol and 4-phenylbutan-1-ol.

Another particularly preferred embodiment according to the invention is a use as defined herein, wherein the one or more iodide salt(s) or hydrate(s) thereof is/are selected from the group consisting of magnesium iodide, magnesium iodide hydrate, potassium iodide, potassium iodide hydrate, ammonium iodide, ammonium iodide hydrate, sodium iodide, sodium iodide hydrate, lithium iodide and lithium iodide hydrate, preferably wherein the iodide salt is sodium iodide, and wherein the one or more inorganic and/or organic acid(s) is/are selected from the group consisting of sulfuric acid, preferably concentrated sulfuric acid, methanesulfonic acid, p-toluenesulfonic acid, preferably p-toluenesulfonic acid monohydrate, and hydrochloric acid, preferably wherein the inorganic and/or organic acid is methanesulfonic acid, and wherein the alcohol of formula (II) is selected from the group consisting of ethanol, 2-phenyl ethanol, (E)-3-phenylprop-2-en-1-ol, hexan-3-ol, 3-methylbut-2-en-1-ol, (E)-hex en-1-ol, (Z)-hex-3-en-1-ol, propan-2-ol, butan-2-ol, 2-methylpropan-1-ol, 2-methylbutan-2-ol, 3-methylbutan-1-ol, 2-methylbutan-1-ol, hexan-2-ol, heptan-1-ol, heptan-2-ol, 2-isopropyl methyl-cyclohexanol, propan-1-ol, butan-1-ol, pentan-1-ol, hexan-1-ol, 3-phenylpropan-1-ol and 4-phenylbutan-1-ol.

Preferred embodiments of the method according to the invention correspond to or can be derived from the preferred embodiments of the use according to the invention which are explained above or vice versa.

The invention will now be described in more detail hereinafter with references to the examples. Further aspects of the present invention are disclosed in the accompanying claims.

EXAMPLES

Example 1: Method According to the Invention for Producing ethyl-2-(4-hydroxy-3-methoxy-phenyl)acetate (17)

17

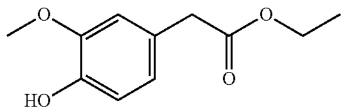

Step (a): To a solution of vanillylmandelic acid (600 g, 3.03 mol) in ethanol (642 g, 13.96 mol) was given sodium iodide (364 g, 2.43 mol), phosphonic acid (248 g, 3.02 mol), and methanesulfonic acid (36.4 g, 0.38 mol) at room temperature. The resulting reaction mixture was then heated for 4 hours at 80° C. while stirring. After cooling to room temperature, 1600 g water and 336 g solid $Na_2SO_3$ were added to the mixture and stirred for an additional 10 minutes. Next, under reduced pressure a water/ethanol mixture was distilled off and the remaining residue was extracted with 800 g MtBE (methyl-tert-butyl ether) and 400 g saturated NaCl solution. The organic phase was finally concentrated under reduced pressure and the product was purified by distillation. Ethyl-2-(4-hydroxy-3-methoxy-phenyl)acetate (17) was isolated as liquid in 85% yield and 97% purity.

Analytical data of the ethyl-2-(4-hydroxy-3-methoxy-phenyl)acetate (17) obtained:

$^1$H-NMR (400 MHz, $CDCl_3$): δ=6.85 (d, J=8.0 Hz, 1H), 6.81 (d, J=2.0 Hz, 1H), 6.76 (dd, J=8.1, 2.0, 1H), 5.62 (s, 1H), 4.15 (q, J=7.1 Hz, 2H), 3.87 (s, 3H), 3.53 (s, 2H), 1.25 (t, J=7.1 Hz, 3H).

$^{13}$C-NMR (100 MHz, $CDCl_3$): δ=171.9, 146.5, 144.7, 125.9, 122.1, 114.4, 111.7, 60.8, 55.9, 41.0, 14.2.

GCMS: m/z (%)=210 [$M^+$] (30), 137 (100), 122 (11), 107 (2), 94 (8), 77 (2), 66 (3), 51 (3), 39 (3), 29 (8).

Example 2: Method According to the Invention for Producing 3-phenylpropyl 2-(4-hydroxy-3-methoxy-phenyl)acetate (22) via Transesterification of ethyl-2-(4-hydroxy-3-methoxy-phenyl)acetate (17)

22

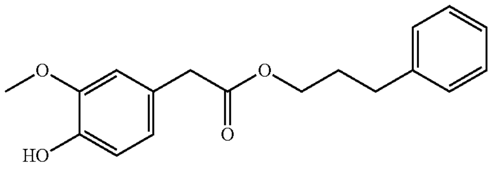

Step (a) of the method is carried out as described in Example 1.

Step (b): To 308 g (1.44 mol) of ethyl-2-(4-hydroxy-3-methoxy-phenyl)acetate (17) were added 235 g (1.73 mol) of 3-phenyl-propan-1-ol and 5.8 g (0.06 mol) of methanesulfonic acid. The reaction mixture was first stirred for 30 minutes under reflux at 200 mbar. Next, the reaction mixture was then stirred under reflux at 150 mbar for 12 hours while ethanol was continuously distilled off. After the addition of 4.3 g (0.04 mol) soda at room temperature, excess 3-phenyl-propan-1-ol as well as remaining amounts of ethyl-2-(4-hydroxy-3-methoxy-phenyl)acetate (17) were distilled off at 1 mbar and 135-175° C. Finally, using a thin film evaporator, 3-phenylpropyl 2-(4-hydroxy-3-methoxy-phenyl)acetate (22) was obtained in 85% yield and 98% purity.

Analytical data of the 3-phenylpropyl 2-(4-hydroxy-3-methoxy-phenyl)acetate (22) obtained:

$^1$H-NMR (600 MHz, $CDCl_3$): δ=7.29-7.24 (m, 2H), 7.20-7.16 (m, 1H), 7.14-7.10 (m, 2H), 6.87 (d, J=8.0 Hz, 1H), 6.81 (d, J=2.0 Hz, 1H), 6.78 (dd, J=8.1, 2.0 Hz, 1H), 5.57 (s, 1H), 4.10 (t, J=6.5 Hz, 2H), 3.88 (s, 3H), 3.54 (s, 2H), 2.64 (dd, J=8.5, 6.8 Hz, 2H), 1.98-1.90 (m, 2H).

$^{13}$C-NMR (151 MHz, $CDCl_3$): δ=171.91, 146.46, 144.75, 141.09, 128.42, 128.37, 126.00, 125.88, 122.13, 114.36, 111.68, 64.10, 55.90, 41.08, 32.06, 30.16.

GC-MS: m/z (%)=300 [M+] (28), 182 (62), 137 (100), 122 (16), 118 (20), 91 (34), 77 (6), 65 (6), 51 (4), 28 (4).

Example 3: Method According to the Invention for Producing the Compound of Formula (III) (methyl-2-(4-hydroxy-3-methoxy-phenyl)acetate)

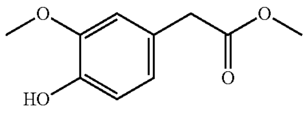

(III)

Step (a): To a solution of vanillylmandelic acid (500 mg, 2.5 mmol) in methanol (1.6 g, 50.5 mmol), sodium iodide (300 mg, 2.0 mmol), phosphonic acid (200 mg, 2.5 mmol) and methanesulfonic acid (400 mg, 3.8 mmol) were added at room temperature. The resulting reaction mixture was then heated for 4 hours at 80° C. while stirring. After cooling to room temperature, 10 g water and 2 g solid $Na_2SO_3$ were added to the mixture and stirred for an additional 10 minutes. Subsequently, methanol was distilled off under reduced pressure and the remaining residue was extracted with 20 g MtBE and 20 g saturated NaCl solution. The organic phase was finally concentrated under reduced pressure and the compound of formula (III) was isolated by silica gel column chromatography (n-hexane/EtOAc, 4:1) in 86% yield and 99% purity.

Analytical data of the compound of formula (III) obtained:

$^1$H-NMR (400 MHz, $CDCl_3$): δ=6.86 (d, J=8.0 Hz, 1H), 6.79 (d, J=1.9 Hz, 1H), 6.76 (ddq, J=8.0, 2.0, 0.5 Hz, 1H), 5.63-5.59 (m, 1H), 3.88 (s, 3H), 3.69 (s, 3H), 3.55 (t, J=0.6 Hz, 2H).

$^{13}$C-NMR (151 MHz, $CDCl_3$): δ=172.4, 146.5, 144.8, 125.7, 122.4, 114.4, 111.73, 55.9, 52.0, 40.8.

Example 4: Method According to the Invention for Producing (2-iso-propyl-5-methyl-cyclohexyl)-2-(4-hydroxy-3-methoxy-phenyl)acetate (16) via Transesterification of the Compound of Formula (III)

16

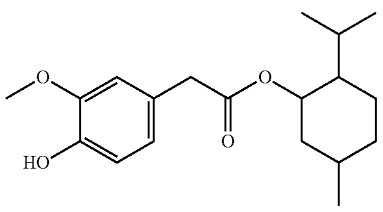

Step (a) of the method is carried out as described in Example 3.

Step (b): To 5 g (25.5 mmol) of compound of formula (III) 4.5 g (28.5 mmol) of 2-isopropyl-5-methyl-cyclohexanol and 0.2 g (2.4 mmol) of methanesulfonic acid were added. The reaction mixture was first stirred for 30 minutes under reflux at 200 mbar. Subsequently, the reaction mixture was stirred under reflux at 150 mbar for 12 hours while methanol was continuously distilled off. After the addition of soda at room temperature, excess 2-isopropyl-5-methyl-cyclohexanol as well as remaining amounts of compound of formula (III) were distilled off at 1 mbar and 170-185° C. Finally, silica gel column chromatography (n-hexane/EtOAc, 5:1) of the residue was performed to obtain (2-iso-propyl-5-methyl-cyclohexyl)-2-(4-hydroxy-3-methoxy-phenyl)acetate (16) in 36% yield and 99% purity.

Analytical data of the (2-iso-propyl-5-methyl-cyclohexyl)-2-(4-hydroxy-3-methoxy-phenyl)acetate (16) obtained:

$^{1}$H-NMR (400 MHz, $CDCl_3$): δ=6.85 (d, J=8.0 Hz, 1H), 6.81 (d, J=2.0 Hz, 1H), 6.76 (dd, J=8.1, 2.0 Hz, 1H), 5.53 (s, 1H), 4.66 (td, J=10.9, 4.4 Hz, 1H), 3.88 (s, 3H), 3.51 (s, 2H), 1.97 (dtd, J=12.0, 3.8, 1.9 Hz, 1H), 1.75 (heptd, j=7.0, 2.7 Hz, 1H), 1.71-1.60 (m, 2H), 1.53-1.40 (m, 1H), 1.36 (ddt, J=12.4, 10.8, 3.2 Hz, 1H), 1.09-1.00 (m, 1H), 0.98-0.92 (m, 1H), 0.89 (d, J=6.5 Hz, 3H), 0.84 (d, J=7.1 Hz, 3H), 0.81 (s, 1H), 0.69 (d, J=7.0 Hz, 3H).

$^{13}$C-NMR (100 MHz, $CDCl_3$): δ=171.5, 146.4, 144.6, 126.2, 122.1, 114.3, 111.6, 74.6, 55.9, 47.1, 41.5, 40.8, 34.2, 31.4, 26.2, 23.4, 22.1, 20.7, 16.3.

Example 5: Method According to the Invention for Producing 2-phenylethyl-2-(4-hydroxy methoxy-phenyl)acetate (1) Via Transesterification of the Compound of Formula (III)

1

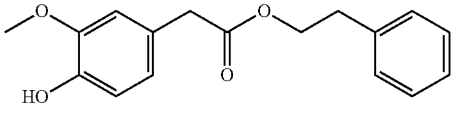

Step (a) of the method is carried out as described in Example 3.

Step (b): To 5 g (25.5 mmol) of compound of formula (III) 3.5 g (28.5 mmol) of 2-phenyl-ethanol and 0.2 g (2.4 mmol) of methanesulfonic acid were added. The reaction mixture was first stirred for 30 minutes under reflux at 200 mbar. Subsequently, the reaction mixture was stirred under reflux at 150 mbar for 12 hours while methanol was continuously distilled off. After the addition of soda at room temperature, excess 2-phenyl-ethanol as well as remaining amounts of compound of formula (III) were distilled off at 1 mbar and 135-175° C. Finally, silica gel column chromatography (n-hexane/EtOAc, 5:1) of the residue was performed to obtain 2-phenylethyl-2-(4-hydroxy-3-methoxy-phenyl)acetate (1) in 82% yield and 99% purity.

Analytical data of the 2-phenylethyl-2-(4-hydroxy-3-methoxy-phenyl)acetate (1) obtained:

$^{1}$H-NMR (400 MHz, $CDCl_3$): δ=7.29-7.24 (m, 2H), 7.24-7.19 (m, 1H), 7.16-7.42 (m, 2H), 6.85 (d, J=7.9 Hz, 1H), 6.74 (d, J=1.9 Hz, 1H), 6.72 (dd, J=8.0, 1.9 Hz, 1H), 5.57 (s, 1H), 4.30 (t, J=6.9 Hz, 2H), 3.84 (s, 3H), 3.51 (s, 2H), 2.91 (t, J=6.9 Hz, 2H).

$^{13}$C-NMR (101 MHz, $CDCl_3$): δ=171.8, 146.4, 144.7, 137.7, 128.9, 128.9, 128.4, 128.4, 126.5, 125.7, 122.2, 114.3, 111.7, 65.3, 55.9, 41.1, 35.0

Example 6: Method According to the Invention for Producing hexyl-2-(4-hydroxy-3-methoxy-phenyl)acetate (21)

21

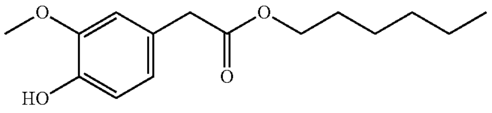

Step (a): To a solution of vanillylmandelic acid (500 mg, 2.5 mmol) in n-hexanol (5.2 g, 50.5 mmol), sodium iodide (300 mg, 2.0 mmol), phosphonic acid (200 mg, 2.5 mmol), and methanesulfonic acid (400 mg, 3.8 mmol) were added at room temperature. The resulting reaction mixture was then heated for 4 hours at 80° C. while stirring. After cooling to room temperature, 10 g water and 2 g solid $Na_2SO_3$ were added to the mixture and stirred for an additional 10 minutes. Subsequently, n-hexanol was distilled off under reduced pressure and the remaining residue was extracted with 20 g MtBE and 20 g saturated NaCl solution. The organic phase was finally concentrated under reduced pressure and hexyl-2-(4-hydroxy-3-methoxy-phenyl)acetate (21) was isolated by silica gel column chromatography (n-hexane/EtOAc, 3:1) in 43% yield and 99% purity.

Analytical data of the hexyl-2-(4-hydroxy-3-methoxy-phenyl)acetate (21) obtained:

$^{1}$H-NMR (400 MHz, $CDCl_3$): δ=6.85 (dd, J=8.1, 0.3 Hz, 1H), 6.81 (d, J=2.0 Hz, 1H), 6.76 (ddq, J=8.1, 2.0, 0.5 Hz, 1H), 5.58 (s, 1H), 4.08 (t, J=6.7 Hz, 2H), 3.86 (s, 3H), 3.53 (s, 2H), 165-1.56 (m, 2H), 1.36-1.2 (m, 6H), 0.87 (t, J=7.0 Hz, 3H).

$^{13}$C-NMR (100 MHz, $CDCl_3$): δ=172.0, 146.5, 144.7, 126.0, 122.1, 114.3, 111.7, 65.0, 55.9, 41.1, 31.4, 28.6, 25.5, 22.5, 14.0.

Example 7: Method According to the Invention for Producing butyl-2-(4-hydroxy-3-methoxy-phenyl)acetate (19)

19

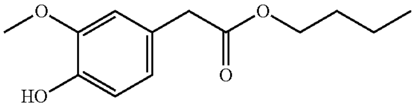

Step (a): To a solution of vanillylmandelic acid (500 mg, 2.5 mmol) in n-butanol (3.8 g, 50.5 mmol), sodium iodide (300 mg, 2.0 mmol), phosphonic acid (200 mg, 2.5 mmol), and methanesulfonic acid (400 mg, 3.8 mmol) were added at room temperature. The resulting reaction mixture was then heated for 4 hours at 80° C. while stirring. After cooling to room temperature, 10 g water and 2 g solid $Na_2SO_3$ were added to the mixture and stirred for an additional 10 minutes. Subsequently, n-butanol was distilled off under reduced pressure and the remaining residue was extracted with 20 g MtBE and 20 g saturated NaCl solution. The organic phase was finally concentrated under reduced pressure and butyl-2-(4-hydroxy methoxy-phenyl)acetate (19) was isolated by silica gel column chromatography (n-hexane/EtOAc, 3:1) in 56% yield and 99% purity.

Analytical data of the butyl-2-(4-hydroxy-3-methoxy-phenyl)acetate (19) obtained:

$^1$H-NMR (400 MHz, $CDCl_3$): δ=6.85 (d, J=8.1 Hz, 1H), 6.81 (dd, J=2.0, 0.5 Hz, 1H), 6.76 (ddt, J=8.1, 1.9, 0.6 Hz, 1H), 5.60 (s, 1H), 4.09 (t, J=6.7 Hz, 2H), 3.87 (d, J=0.3 Hz, 3H), 3.53 (t, J=0.5 Hz, 2H), 1.67-1.55 (m, 2H), 1.42-1.29 (m, 2H), 0.91 (t, J=7.4 Hz, 3H).

$^{13}$C-NMR (101 MHz, $CDCl_3$): δ=172.0, 146.5, 144.7, 126.0, 122.1, 114.3, 111.7, 64.7, 55.9, 41.1, 30.6, 19.1, 13.7.

Example 8: Method According to the Invention for Producing 2-methylbutyl-2-(4-hydroxy-3-methoxy-phenyl)acetate (12)

12

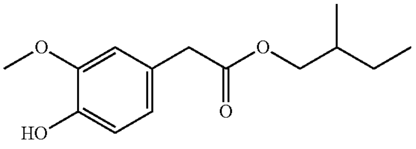

Step (a): To a solution of vanillylmandelic acid (500 mg, 2.5 mmol) in 2-methylbutan-1-ol (3.0 g, 34.0 mmol), sodium iodide (300 mg, 2.0 mmol), phosphonic acid (200 mg, 2.5 mmol), and methanesulfonic acid (400 mg, 3.8 mmol) were added at room temperature. The resulting reaction mixture was then heated for 4 hours at 80° C. while stirring. After cooling to room temperature, 10 g water and 2 g solid $Na_2SO_3$ were added to the mixture and stirred for an additional 10 minutes. Subsequently, 2-methylbutan-1-ol was distilled off under reduced pressure and the remaining residue was extracted with 20 g MtBE and 20 g saturated NaCl solution. The organic phase was finally concentrated under reduced pressure and 2-methylbutyl-2-(4-hydroxy-3-methoxy-phenyl)acetate (12) was isolated by silica gel column chromatography (n-hexane/EtOAc, 3:1) in 49% yield and 99% purity.

Analytical data of the 2-methylbutyl-2-(4-hydroxy-3-methoxy-phenyl)acetate (12) obtained:

$^1$H-NMR (400 MHz, $CDCl_3$): δ=6.86 (d, J=8.1 Hz, 1H), 6.81 (d, J=2.0 Hz, 1H), 6.77 (dd, J=8.0, 2.0 Hz, 1H), 5.55 (s, 1H), 3.97 (dd, J=10.7, 6.0 Hz, 1H), 3.90 (dd, J=10.8, 6.7 Hz, 1H), 3.88 (s, 3H), 3.54 (s, 2H), 1.69 (dddd, J=12.4, 7.8, 6.8, 5.8 Hz, 1H), 1.38 (dtd, J=13.1, 7.5, 5.6 Hz, 1H), 1.23-1.08 (m, 1H), 0.88 (d, J=6.8 Hz, 3H), 0.88 (t, J=7.5 Hz, 3H).

$^{13}$C-NMR (100 MHz, $CDCl_3$): δ=172.0, 146.4, 144.7, 126.0, 122.1, 114.3, 111.7, 69.4, 55.9, 41.1, 34.1, 26.0, 16.3, 11.2.

Example 9: Method According to the Invention for Producing ethyl-2-(4-hydroxy-3-methoxy-phenyl)acetate (17)

17

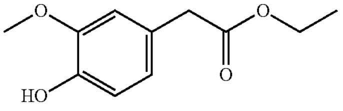

Step (a): Sodium iodide (500 mg, 12.6 mmol), phosphonic acid (4.2 g, 50.5 mmol), and 4-methylbenzenesulfonic acid (9.6 g, 50.5 mmol) were added at room temperature to a solution of vanillylmandelic acid (5 g, 25.2 mmol) in ethanol (23 g, 514.7 mmol). The resulting reaction mixture was heated for 4 hours at 80° C. while stirring. After cooling to room temperature, 160 g water and 30 g solid $Na_2SO_3$ were added to the mixture and stirred for an additional 10 minutes. Subsequently, a water/ethanol mixture was distilled off under reduced pressure and the remaining residue was extracted with 100 g MtBE and 40 g saturated NaCl solution. The organic phase was finally concentrated under reduced pressure and the ethyl-2-(4-hydroxy-3-methoxy-phenyl)acetate (17) was isolated by silica gel column chromatography (n-hexane/EtOAc, 3:1) in 91% yield and 98% purity.

Example 10: Method According to the Invention for Producing ethyl-2-(4-hydroxy-3-methoxy-phenyl)acetate (17)

17

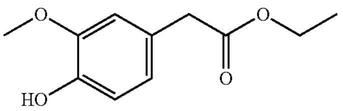

Step (a): Magnesium iodide (2.1 g, 7.6 mmol), phosphonic acid (4.2 g, 50.5 mmol), and 4-sulfuric acid (4.9 g, 50.5 mmol) were added at room temperature to a solution of vanillylmandelic acid (5 g, 25.2 mmol) in ethanol (23 g, 514.7 mmol). The resulting reaction mixture was heated for 4 hours at 80° C. while stirring. After cooling to room temperature, 160 g water and 30 g solid $Na_2SO_3$ were added to the mixture and stirred for an additional 10 minutes. Subsequently, a water/ethanol mixture was distilled off under reduced pressure and the remaining residue was extracted with 100 g MtBE and 40 g saturated NaCl solution. The organic phase was finally concentrated under reduced pressure and the ethyl-2-(4-hydroxy methoxy-phenyl)acetate (17) was isolated by silica gel column chromatography (n-hexane/EtOAc, 3:1) in 79% yield and 99% purity.

Example 11: Method According to the Invention for Producing ethyl-2-(4-hydroxy-3-methoxy-phenyl)acetate (17)

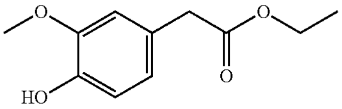

17

Step (a): Potassium iodide (2.1 g, 7.6 mmol), phosphonic acid (4.2 g, 50.5 mmol), and 4-methanesulfonic acid (4.8 g, 50.5 mmol) were added at room temperature to a solution of vanillylmandelic acid (5 g, 25.2 mmol) in ethanol (23 g, 514.7 mmol). The resulting reaction mixture was heated for 4 hours at 80° C. while stirring. After cooling to room temperature, 160 g water and 30 g solid $Na_2SO_3$ were added to the mixture and stirred for an additional 10 minutes. Subsequently, a water/ethanol mixture was distilled off under reduced pressure and the remaining residue was extracted with 100 g MtBE and 40 g saturated NaCl solution. The organic phase was finally concentrated under reduced pressure and the ethyl-2-(4-hydroxy methoxy-phenyl)acetate (17) was isolated by silica gel column chromatography (n-hexane/EtOAc, 3:1) in 82% yield and 97% purity.

The invention claimed is:

1. A method for producing a compound of formula (I) or a physiologically acceptable salt thereof comprising:

(I)

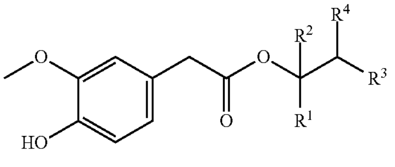

(a) simultaneously reacting vanillylmandelic acid and/or a physiologically acceptable salt thereof with:
one or more iodide salts or hydrates thereof,
one or more reducing agents,
one or more inorganic and/or organic acids other than phosphonic acid, and
methanol and/or a physiologically acceptable salt thereof or an alcohol of formula (II) and/or a physiologically acceptable salt thereof:

(II)

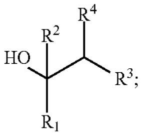

and (b) provided that methyl-2-(4-hydroxy-3-methoxy-phenyl) acetate of formula (III) and/or a physiologically acceptable salt thereof is obtained in (a), (III)

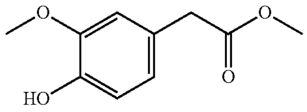

subjecting the compound of formula (III) and/or physiologically acceptable salt thereof and an alcohol of formula (II) and/or a physiologically acceptable salt thereof to a transesterification reaction to obtain a compound of formula (I) and/or a physiologically acceptable salt thereof, or
provided that a compound of formula (I) and/or a physiologically acceptable salt thereof is obtained in (a), optionally subjecting the compound of formula (I) and/or salt thereof obtained in (a) and an alcohol of formula (II) that is different from the alcohol of formula (II) of (a) and/or a physiologically acceptable salt thereof to a transesterification reaction,
wherein in the compound of formula (I) and in the alcohol of formula (II), respectively,
(i) $R^1$ and $R^2$ independently represent hydrogen or an alkyl residue with 1-2 carbon atoms, and
$R^3$ and $R^4$ independently represent a residue selected from hydrogen, linear or branched alkyl with 1-5 carbon atoms, phenyl, alkylphenyl, phenylalkyl, linear or branched alkenyl with 2-4 carbon atoms, alkenylphenyl, and phenylalkenyl, or
(ii) $R^1$ and $R^3$ form a cyclohexyl ring together with carbon atoms that link them, the cyclohexyl ring optionally carrying a residue $R^5$, wherein $R^5$ represents an alkyl residue with 1-2 carbon atoms, and $R^2$ represents hydrogen or an alkyl residue with 1-2 carbon atoms, and
$R^4$ represents a residue selected from hydrogen, linear or branched alkyl with 1-5 carbon atoms, phenyl, alkylphenyl, phenylalkyl, linear or branched alkenyl with 2-4 carbon atoms, alkenylphenyl, and phenylalkenyl.

2. The method of claim 1, wherein a total amount of 0.1-1 equivalents of the one or more iodide salts or hydrates thereof is reacted in (a) based on 1 equivalent of the vanillylmandelic acid and/or salt thereof.

3. The method of claim 1, wherein a total amount of 0.5-2 equivalents of the one or more reducing agents is reacted in (a) based on 1 equivalent of the vanillylmandelic acid and/or salt thereof.

4. The method of claim 1, wherein a total amount of 0.1-2 equivalents of the one or more inorganic and/or organic acids is reacted in (a) based on 1 equivalent of the vanillylmandelic acid and/or salt thereof.

5. The method of claim 1, wherein a total amount of 2-20 equivalents of the methanol and/or salt thereof or alcohol of formula (II) and/or salt thereof is reacted in (a) based on 1 equivalent of the vanillylmandelic acid and/or salt thereof.

6. The method of claim 1, wherein the one or more iodide salts or hydrates thereof are selected from magnesium iodide, magnesium iodide hydrate, potassium iodide, potassium iodide hydrate, ammonium iodide, ammonium iodide hydrate, sodium iodide, sodium iodide hydrate, lithium iodide, and lithium iodide hydrate.

7. The method of claim 1, wherein the one or more inorganic and/or organic acids are selected from sulfuric acid, methanesulfonic acid, and p-toluenesulfonic acid.

8. The method of claim 1, wherein the alcohol of formula (II) is selected from ethanol, 2-phenylethanol, (E)-3-phenylprop-2-en-1-ol, hexan-3-ol, 3-methylbut-2-en-1-ol, (E)-hex-2-en-1-ol, (Z)-hex-3-en-1-ol, propan-2-ol, butan-2-ol, 2-methylpropan-1-ol, 2-methylbutan-2-ol, 3-methylbutan-1-ol, 2-methylbutan-1-ol, hexan-2-ol, heptan-1-ol, heptan-2-ol, 2-isopropyl-5-methyl-cyclohexanol, propan-1-ol, butan-1-ol, pentan-1-ol, hexan-1-ol, 3-phenylpropan-1-ol, and 4-phenylbutan-1-ol.

9. The method of claim 1, wherein the compound of formula (I) and/or a physiologically acceptable salt thereof is incorporated into a pharmaceutical preparation, or into a preparation used in nutrition, oral hygiene, or consumed for pleasure.

10. A method for converting vanillylmandelic acid and/or a physiologically acceptable salt thereof into a compound of formula (I) and/or a physiologically acceptable salt thereof or into methyl-2-(4-hydroxy-3-methoxy-phenyl) acetate of formula (III) and/or a physiologically acceptable salt thereof comprising:

(I)

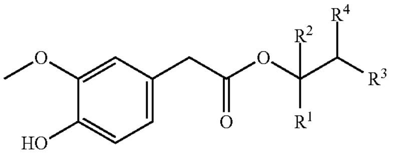

(III)

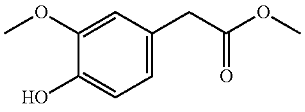

simultaneously combining:

one or more iodide salts or hydrates thereof, one or more reducing agents, one or more inorganic and/or organic acids other than phosphonic acid, and methanol and/or a physiologically acceptable salt thereof or an alcohol of formula (II) and/or a physiologically acceptable salt thereof (II)

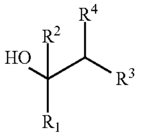

wherein in the compound of formula (I) and in the alcohol of formula (II), respectively, (i) $R^1$ and $R^2$ independently represent hydrogen or an alkyl residue with 1-2 carbon atoms, and $R^3$ and $R^4$ independently represent a residue selected from hydrogen, linear or branched alkyl with 1-5 carbon atoms, phenyl, alkylphenyl, phenylalkyl, linear or branched alkenyl with 2-4 carbon atoms, alkenylphenyl, and phenylalkenyl, or (ii) $R^1$ and $R^3$ form a cyclohexyl ring together with carbon atoms that link them, the cyclohexyl ring optionally carrying a residue $R^5$, wherein $R^5$ represents an alkyl residue with 1-2 carbon atoms, and $R^2$ represents hydrogen or an alkyl residue with 1-2 carbon atoms, and $R^4$ represents a residue selected from hydrogen, linear or branched alkyl with 1-5 carbon atoms, phenyl, alkylphenyl, phenylalkyl, linear or branched alkenyl with 2-4 carbon atoms, alkenylphenyl, and phenylalkenyl.

11. The method of claim 10, wherein a total amount of 0.1-1 equivalents of the one or more iodide salts or hydrates thereof is used based on 1 equivalent of the vanillylmandelic acid and/or salt thereof.

12. The method of claim 10, wherein a total amount of 0.5-2 equivalents of the one or more reducing agents is used based on 1 equivalent of the vanillylmandelic acid and/or salt thereof.

13. The method of claim 10, wherein a total amount of 0.1-2 equivalents of the one or more inorganic and/or organic acids is used based on 1 equivalent of the vanillylmandelic acid and/or salt thereof.

14. The method of claim 10, wherein a total amount of 2-20 equivalents of the methanol and/or salt thereof or alcohol of formula (II) and/or salt thereof is used based on 1 equivalent of the vanillylmandelic acid and/or salt thereof.

15. The method of claim 10, wherein the one or more iodide salts or hydrates thereof are selected from magnesium iodide, magnesium iodide hydrate, potassium iodide, potassium iodide hydrate, ammonium iodide, ammonium iodide hydrate, sodium iodide, sodium iodide hydrate, lithium iodide, and lithium iodide hydrate, the one or more inorganic and/or organic acid(s) is/are selected from the group consisting of sulfuric acid, and/or the alcohol of formula (II) is selected from ethanol, 2-phenylethanol, (E)-3-phenylprop-2-en-1-ol, hexan-3-ol, 3-methylbut-2-en-1-ol, (E)-hex-2-en-1-ol, (Z)-hex-3-en-1-ol, propan-2-ol, butan-2-ol, 2-methylpropan-1-ol, 2-methylbutan-2-ol, 3-methylbutan-1-ol, 2-methylbutan-1-ol, hexan-2-ol, heptan-1-ol, heptan-2-ol, 2-isopropyl-5-methyl-cyclohexanol, propan-1-ol, butan-1-ol, pentan-1-ol, hexan-1-ol, 3-phenylpropan-1-ol, and 4-phenylbutan-1-ol.

16. The method of claim 1, wherein the one or more reducing agents is phosphonic acid.

17. The method of claim 1, wherein a total amount of 0.35-0.85 equivalents of the one or more iodide salts or hydrates thereof is reacted in (a) based on 1 equivalent of the vanillylmandelic acid and/or salt thereof.

18. The method of claim 1, wherein a total amount of 0.9-1.2 equivalents of the one or more reducing agents is reacted in (a) based on 1 equivalent of the vanillylmandelic acid and/or salt thereof, and wherein the one or more reducing agents comprise phosphonic acid.

19. The method of claim 1, wherein a total amount of 0.3-1.5 equivalents of the one or more inorganic and/or organic acids is reacted in (a) based on 1 equivalent of the vanillylmandelic acid and/or salt thereof.

20. The method of claim 1, wherein a total amount of 4-12 equivalents of the methanol and/or salt thereof or alcohol of formula (II) and/or salt thereof is reacted in (a) based on 1 equivalent of the vanillylmandelic acid and/or salt thereof.

* * * * *